United States Patent [19]

Monthony

[11] 4,246,222
[45] Jan. 20, 1981

[54] GEL SLAB CASTING

[75] Inventor: James F. Monthony, Albany, Calif.

[73] Assignee: Bio-Rad Laboratories, Inc., Richmond, Calif.

[21] Appl. No.: 87,196

[22] Filed: Oct. 22, 1979

[51] Int. Cl.³ .............................................. B29C 1/02
[52] U.S. Cl. ................................... 264/219; 264/259; 264/261; 264/299; 264/334
[58] Field of Search .............. 264/259, 265, 299, 334, 264/261, 219; 204/180 G, 299 R

[56] References Cited

U.S. PATENT DOCUMENTS

| 3,964,992 | 6/1979 | Krotz | 204/180 G |
| 3,980,540 | 9/1976 | Haefer | 204/180 G |
| 3,988,320 | 10/1976 | Krotz | 204/180 G |
| 4,151,065 | 4/1979 | Kaplan | 204/180 G |

Primary Examiner—Sam Silverberg
Attorney, Agent, or Firm—Townsend and Townsend

[57] ABSTRACT

A method and apparatus for casting gel slabs useful in electrophoretic procedures is provided. Glass plates are horizontally positioned in parallel a capillary action-inducing distance apart to form an unsealed space. Gel-forming liquid, e.g. polyacrylamide is introduced between the plates and fills the space by capillary action. The surface tension of the gel-forming liquid is utilized to constrain the liquid between the plates at the unsealed or open edges. Once the desired sized space is filled the gel is formed by polymerization and/or cooling. Where an open faced gel slab is desired one of the plates is separated from the gel layer.

8 Claims, 5 Drawing Figures

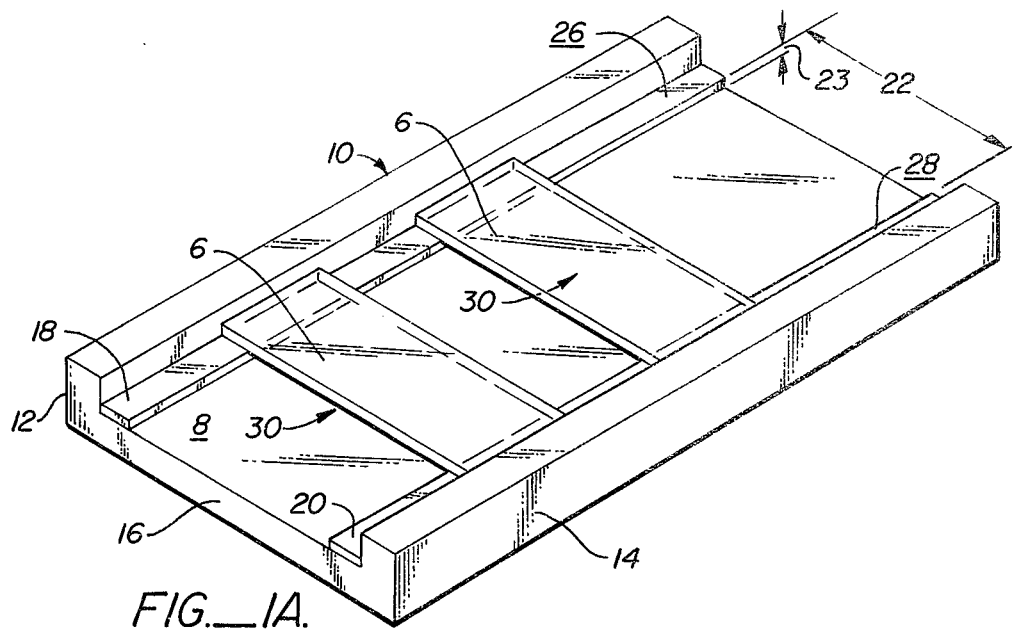
FIG._1A.
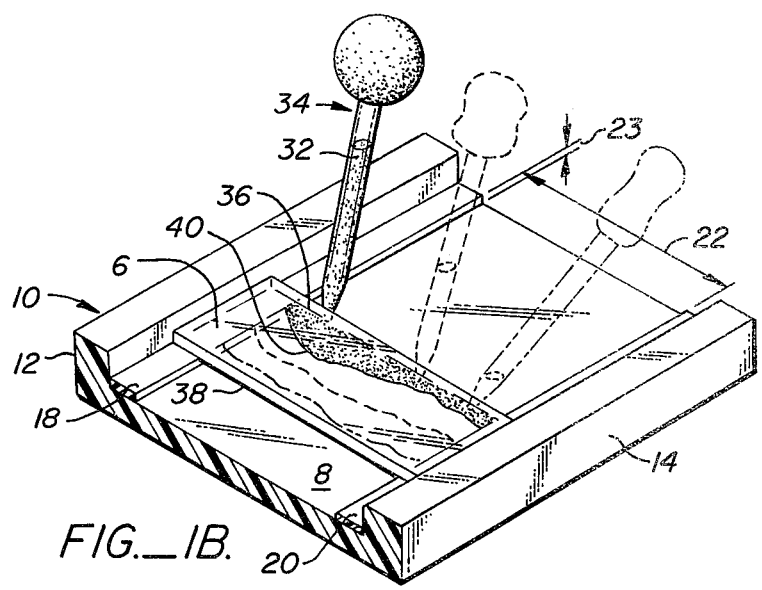
FIG._1B.
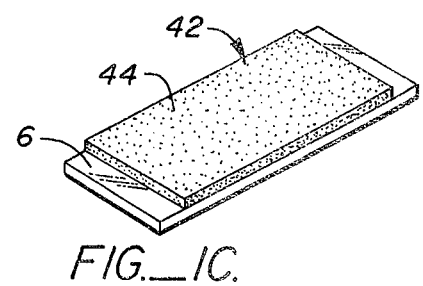
FIG._1C.

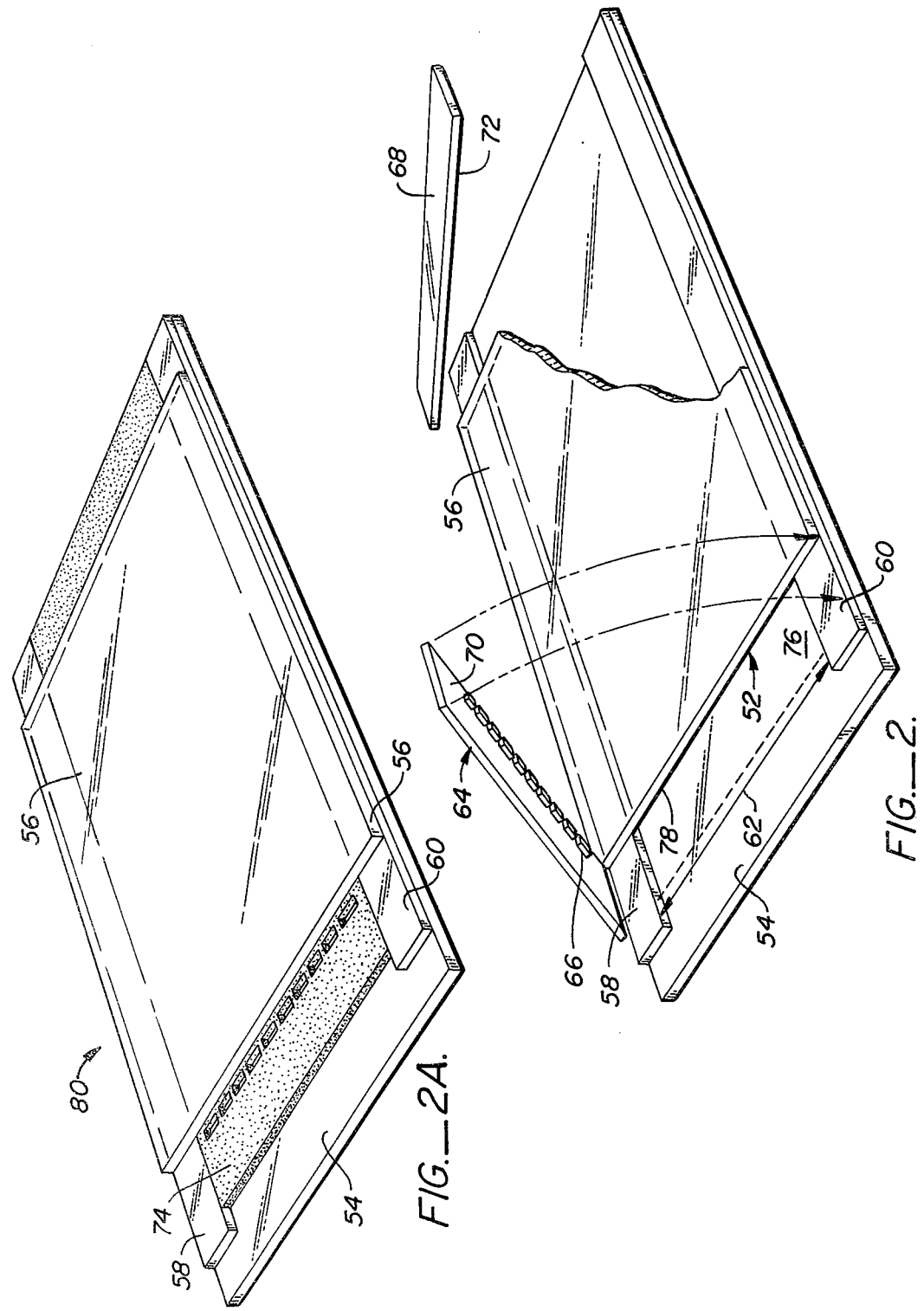

GEL SLAB CASTING

This invention relates to a method and apparatus for the preparation of gel slabs useful for electrophoretic procedures.

BACKGROUND OF THE INVENTION

Gel electrophoresis is a well known method for separation and analysis of proteins, nucleic acids and other charged species. For purposes of this application by electrophoresis is meant the category of separation methods which utilizes an applied voltage to cause migration of charged species in an anti-convection medium, including but not limited to electrophoresis, immunoelectrophoresis, SDS (sodium dodecylsulfate) electrophoresis, isoelectric focusing, affinoelectrophoresis, 2-dimensional electrophoresis and the like.

Many electrophoretic procedures are advantageously performed in thin layers of gel on glass plates. For convenience the gel layer is pre-cast into a rectangular shape of uniform thickness affixed to a glass plate substrate of substantially the same size. The pre-cast gel covered glass surface, i.e. gel slab, frequently has a series of uniform indentations or sample wells aligned in a row at one end of the plate where samples of the substances to be electrophoresed are deposited. Uniformity in the thickness of the gel layer except where there are sample wells is an important characteristic of the gel slabs.

The use of polyacrylamide as the gel is particularly advantageous for many procedures and a variety of methods to produce such polyacrylamide gel plates have been developed. Typically, a monomer solution or other gel forming liquid is first brought in contact with its glass substrate and then polymerized or allowed to set into a relatively solid, non-flowable state. The inhibition of the polymerization of acrylamide monomer solutions by oxygen is well known. As such, acrylamide solutions are typically degassed under vacuum to remove any dissolved oxygen and then polymerized in a substantially sealed apparatus.

Various methods of casting gel slabs are known. Where the gel-forming liquid is other than polyacrylamide it is known to position a glass plate between parallel spacer rails having raised edges, the height of the edge corresponding to the thickness of the gel layer desired, to place gel-forming liquid in the center of the plate, and to smear the liquid across the entire plate using a straight edge. Such a method is not useful for casting polyacrylamide gel slabs since the acrylamide monomer will not polymerize in an apparatus wherein the liquid layer is openfaced and exposed to air. As such, separate equipment would be required for preparing polyacrylamide gel slabs and a typical laboratory which requires all varieties of gel slabs would experience duplicative equipment costs.

Whenever polyacrylamide is the gel-forming liquid, prior art procedures have required that the monomer solution be introduced into a space between plates sealed by a gasket around the edges, except for the edge into which the monomer is introduced. Typically two glass plates are separated by a rubber gasket interjected between the four edges and held together and sealed by a series of adjacent clamps. The thin space thus formed is then placed in a vertical position and monomer is introduced at one corner where the gasket is displaced. After the space is filled the remaining portion of the gasket is put in place and clamped. The monomer solution is then polymerized in place by procedures known in the art, e.g. by exposure to polymerizing light, heat or the like, depending upon the cross-linking agent and/or initator present in the solution.

Known methods of casting polyacrylamide gel slabs require cumbersome apparatus for constructing sealed spaces. Moreover, a separate sealed space must be formed for each such slab to be cast. Where molds are provided which hold more than one set of plates in an upright position each set of plates must be of equal dimensions. Where only a single sample is to be tested and thus only a narrow portion of the full sized plate is to be utilized, the experimenter has only the options of under-utilizing the plate formed or cutting it into appropriately sized strips. A further difficulty with the known procedures of gel slab preparation is that non-uniform gel layer thickness can result from uneven pressure on the plates, such as from unequal tightening of various clamps.

Accordingly there is a need for a simplified and less cumbersome method and apparatus for casting gel slabs which is applicable to the various gel-forming liquids used in electrophoretic procedure. Additionally there is a need for a method and apparatus which is easy and inexpensive and by which multiple gel slabs of varying dimensions can be simultaneously or sequentially cast.

SUMMARY OF THE INVENTION

The present invention provides a method and apparatus for preparing polyacrylamide gel slabs of varying sizes without the need for a clamps, gaskets or the like. Broadly, the invention utilizes capillary action to fill an unsealed space between the opposed surfaces of two parallel, spaced, horizontally positioned plates. By the method of the present invention, the plates are horizontally positioned in parallel a capillary action-inducing distance apart; gel-forming liquid is introduced between the plates at one open edge in a manner which produces a moving front of liquid attracted by capillary action to flow across and fill the space between the plates. The surface tension of the gel-forming liquid is utilized to constrain the gel-forming liquid between the plates at the unsealed or open edges of the space between the plates. Once the desired space is filled with gel-forming liquid, the gel is formed by polymerization and/or by cooling.

BRIEF DESCRIPTION OF THE DRAWINGS

FIG. 1A is a perspective view depicting one embodiment of apparatus utilized in the present invention after the space to be filled by gel-forming liquid has been formed.

FIG. 1B is a perspective view of a portion of the apparatus of FIG. 1A depicting the gel forming liquid being introduced and the movement of the front of flowing liquid under the upper plate.

FIG. 1C is a perspective view of a gel slab formed on the apparatus of FIG. 1A.

FIG. 2 is a perspective view of apparatus constructed according to a second embodiment of the present invention.

FIG. 2A depicts the gel slab prepared on the apparatus of FIG. 2.

DESCRIPTION OF THE PREFERRED EMBODIMENTS

One embodiment of the present invention is a method by which one or more gel slabs, of equal length and of the same or varying widths, are cast by adhering a gel layer to each glass plate. According to the present invention, for each slab to be cast, an open-edged space of substantially the same dimensions as the gel layer to be made is formed between a glass plate 6 and the portion of the bottom surface 8 of a casting tray 10 which is coextensive with the plate 6, as depicted in FIG. 1A. The casting tray 10 comprises a bottom wall 16 with an upwardly facing planar surface 8 and two opposed, longitudinal side walls 12, 14 extending upwardly therefrom. The casting tray 10 may optionally have similar opposed end walls (not shown).

Residing in the casting tray 10 on the bottom surface 8 are two elongated spacer rails 18, 20. The spacer rails 18, 20 are typically, but not necessarily, positioned along the side walls 12, 14 of the casting tray 10. The only requirements are (1) that the spacer rails 18, 20 be spaced, preferably in parallel, a predetermined distance 22 apart and (2) that the vertical distance 23 between the glass plate 6 and the bottom surface 8 of the casting tray 10 be uniform and that the vertical distance 23 from the bottom surface 8 of the bottom wall 16 of the casting tray 10 to the upward facing surfaces 26, 28 of each rail 18, 20 be of equal magnitude. Thus, the thickness of each of the spacer rails 18, 20 is substantially equal to the thickness of the other.

In the practice of the present invention, spaces substantially equivalent in size to the gel layer of the desired gel slab are formed in the apparatus as depicted in FIGS. 1A and 1B. One or more rectangular glass plates 6, such as slides, are positioned, typically at spaced intervals, extending between the longitudinal side walls 12, 14 to span across the distance 22 between the two spacer rails 18, 20. Preferably, the glass plates 6 will have a length sufficient to abut the insides of the longitudinal side walls 12, 14 of the casting tray 10 whereby the plate is easily aligned. By positioning the plates 6 as depicted in FIG. 1A, openedged spaces 30 are formed between the glass plates 6 and coextensive portions of the bottom surface 8 of the bottom wall 16.

A gel-forming liquid, typically a monomer or agarose solution, is then introduced into the spaces 30 at one of the open edges thereof. The vertical distance 23 between glass plates 6 and the bottom surface 8 of the bottom wall 16 of the tray 10 is of such a magnitude as to induce capillary action with regard to the gel forming liquid and thus as the gel-forming liquid is introduced into the open edged space 30 at a first edge 36, it flows across the space 30 and fills it rapidly by capillary action. Surface tension prevents the gel-forming liquid from flowing beyond the edges 36, 38 of the glass plate 6, i.e. confines the liquid to space 30.

Gel-forming liquids of the present invention are typically any of those which form gels useful for electrophoretic procedures. Most often the liquids are agarose solutions, i.e. water solutions of agarose, a linear polysaccharide soluble in warm water which forms a gel upon cooling, or monomer and monomer/buffer solutions (referred to as monomer solutions) typically comprising from 1.0 to about 20% by weight of acrylamide or other monomer in water.

For purposes of the present invention, the gel-forming liquids have substantially the same properties as 80–100% water solutions with regard to capillary action, i.e. the force of adhesion existing between the liquid and a solid in capillarity. In other words, gel-forming liquids of the present invention are those which behave substantially the same as water in their attractive force or molecular attraction for solid surfaces. Similarly, gel-forming liquids of the present invention exhibit substantially the same surface tension, i.e. contracting surface force tending to minimize the surface area of a liquid, as water. Where necessary to the formation of a gel, the gel-forming liquid, e.g. monomer solution, will include a cross-linking agent and/or initiating agent for effecting curing or polymerization of the liquid to form a solid or semi-solid. i.e. gel. As will be known and understood by those skilled in the art, any number of other additives may be present in this gel-forming liquid as required for gel characteristics desired for particular electrophoretic procedures, including but not limited to buffers, such as 2-amino, 2-hydroxymethyl, 1,3 propanediol (TRIS) and its hydrochloride salt, TRIS-glycine, sodium borate, or acetic acid buffers.

One preferred monomer solution comprises 5 percent by weight acrylamide, 0.15 percent by weight bis(N,N' methylene-bis-acrylamide), 0.0005 percent by weight riboflavin-5' phosphate, 2.0 percent by weight of Biolyte TM 3-10 ampholyte. Polymerization of this monomer solution is effected by exposure to polymerizing light at a wavelength of 350 to 500 NM.

Similarly, the percent monomer may be varied to obtain whatever gel characteristics, e.g. porosity, are desired for the specific procedure to be carried out. Variations in the composition of the solution will change the liquid characteristics, i.e. capillarity and surface tension, to a certain degree but the desired capillary action and surface tension will be present in and between gel-forming liquids of the present invention and solid surfaces spaced apart at a capillary action-inducing distance, preferably about 0.25 mm to about 3.5 mm.

A capillary action inducing distance is the distance between two solid surfaces which will draw in a gel-forming liquid therebetween due to the attractive forces between the liquid and solid surfaces. It is believed that by spacing the glass plate and bottom surface of the casting tray a capillary action inducing distance apart, the monomer solution front 40 is drawn into the space 30 and moves throughout the space 30 while maintaining a substantially vertical interface with the air being expelled. When the monomer front reaches the opposite open edge, the forces associated with its being in capillarity with the solid surfaces in conjunction with its own surface tension, keep the monomer from flowing beyond the defined space. In contrast, monomer solution introduced between two surfaces spaced apart a non-capillary action inducing distance will continue to seek its own level flowing beyond the open edges of the defined space. Even if dammed along the open edge, the monomer front would establish an essentially horizontal interface with the air being expelled. Additionally, monomer solution introduced at the edge of two surfaces spaced a non-capillary action inducing distance will not be drawn into the space as in the present invention but will likely flow equally in both directions from the edge, i.e. no surface tension will be established to confine the liquid to the defined space.

As depicted in FIG. 1B, monomer solution 32 is introduced, e.g. by pipette 34, along a first open edge 36 of the space 30 between the glass plate 6 and the bottom surface 8 and is drawn into the space by capillary action. A monomer front 40 between the plate 6 and the bottom surface 8 extending the distance 22 between the spacer rails 18, 20 is formed by introducing the solution, e.g. by moving the pipette, along the length of the edge 36 as depicted. As monomer solution 32 continues to be introduced along the first open edge 36, the front 40 continues to be drawn by capillary action between the glass plate 6 and the bottom surface 8 toward the opposite second edge 38 and thus the space 30 is filled, the air being expelled out the opposite edge 38, with no air bubbles being trapped. Sufficient monomer solution 32 is introduced to fill the space 30 between the glass plate 6 and the coextensive portion of the bottom surface 8, i.e. the volume defined by the area of the bottom surface 8 coextensive with the glass plate 6 times the distance 23 equal to the thickness of the spacer rails 18, 20.

A gel layer is then formed by polymerizing the monomer solution 32 in place. Formation of the gel layer is carried out by exposing the monomer solution to heat or light depending upon the particular monomer and/or initiator present in the monomer solution. Where the gel-forming liquid is an agarose solution a gel layer is formed by cooling the liquid confined between the surfaces of plate 6 and bottom wall surface 8.

A gel slab 42 shown in FIG. 1C comprising the glass plate 6 with gel layer 44 adhered thereto is separated from the bottom surface 8 and removed from the casting tray 10. The gel slab 42 may then be stored or used. Separation of the gel slab may be effected by prying, i.e. by inserting a spatula or other flat edge at one open edge between the gel layer and the bottom surface so that air may slowly penetrate through the channel made by the spatula and then exerting an upward prying force on the glass plate. Preferably, the bottom surface of the casting tray is made of a material less adherent to the gel than glass, such as Teflon ® or acrylic, or is coated with a release agent, such as silicone, in which case the gel slab may be separated from the casting tray by pulling the glass plate upwardly at one or both edges.

When more than one glass plate simultaneously span the distance 22 between the spacer rails 18, 20 as depicted in FIG. 1A, a plurality of gel slabs may be formed by sequentially introducing gel forming liquid into the spaces formed between the glass plates and their respective coextensive portions of the bottom surface of the casting tray, forming the gel and removing the gel-layered glass plates, i.e. gel slabs, from the casting tray. Gel slabs of various sized areas are formed by varying the widths of the glass plates which span the two spacer rails.

A second embodiment of apparatus useful in practicing the present invention is depicted in FIG. 2 whereby a glass-sandwiched gel layer useful for certain procedures is formed. Typically, such a sandwich will have an area of exposed gel at one end for wicking purposes, i.e. for placement of an electrolyte-carrying wick or other electrical contact and optionally a series of indentations or sample wells across an exposed area at the opposite end.

In FIG. 2 a space 52 is formed by placing a first bottom glass plate 54 and a smaller second top glass plate 56 in parallel, spaced relation separated by two elongated spacer rails 58, 60. The spacer rails 58, 60 are typically, but not necessarily, positioned along the longitudinal edges of the bottom glass plate 54. The requirements regarding the spacer rails 60, 58 are the same as for spacer rails 18, 20 described in FIG. 1A.

Where sample wells are desired, a well-forming bar 64 is disposed along and adjacent to one edge of the upper plate 56 to span the distance 62 between the spacer rails 58, 60. The well-forming bar 64 has a series of teeth or well formers 66 in a straight line which form reciprocal indentations or wells in the gel layer to be formed.

Disposed adjacent to the opposite edge of the top glass plate 56, spanning the distance 62 between the spacer rails 58, 60 is a wick area forming bar 68. In the preferred embodiment the gel-exposed sides of both the well-forming bar 64 and the wick area forming bar 68 comprise a material which exhibits less adherence to the gel than does glass, i.e. Teflon ® or acrylic or have coated on their respective gel-exposed surfaces 70, 72 a release agent, such as silicone.

A continuous gel layer 74 is formed in the space 52 between upward facing surface 76 of the bottom glass plate 54 and the gel exposed surface 70 of the well-forming bar 64, the gel-exposed surface 78 of the top glass plate 56 and the gel-exposed surface 72 of the wick area forming bar 68, by the method of introducing the gel forming liquid into said space as described with respect to FIGS. 1A–B. The well-forming bar 64 and the wick area forming bar 68 are then separated from the gel layer 74, leaving a glass-sandwiched gel 80 ready for use or storage.

In an alternative embodiment (not depicted) a porous paper strip or other contact may be placed in the portion of space 52 between the wick area forming bar 68 and the bottom glass plate 54 prior to introducing the gel-forming liquid therein. The result is an contact imbedded in the gel layer which may be utilized to facilitate completion of any number of well-known electric circuit means used in electrophoretic procedures. Further, such porous strips may be substituted for non-porous spacer rails.

What is claimed is:

1. A method of casting a gel slab useful in electrophoretic procedures, comprising the steps of
   (a) forming a space having first and second opposing open edges between the facing surfaces of parallel horizontally positioned upper and lower plates separated a predetermined capillary action-inducing distance apart;
   (b) introducing a gel forming liquid into said space at one of said open edges whereby said liquid is an amount substantially equal in volume to the volume of said space along the entirety of said first opposing edge in a manner which produces a front of said liquid, said front being drawn into said space by capillary action thereby displacing and expelling air out said second opposing open edge and is contained therein by surface tension; and
   (c) forming from said liquid a gel adhered to at least one of said surfaces.

2. The method of claim 1 wherein one of said surfaces is relatively non-adherent to said gel; and
   further comprising the step of
   (d) releasing said gel from said non-adherent surface.

3. A method according to claim 1 wherein said step of forming further comprises forming said space between one lower plate and at least first, second and third contiguous upper plates.

4. A method according to claim 3 wherein said first and said third upper plates, each contiguous to said second upper plate have relatively non-gel-adherent surfaces opposing said lower plate, and further comprising the step of removing said non-adherent surfaces from said gel.

5. A method according to claim 4 wherein said first upper plate is a sample well forming bar, and said gel-forming step further comprises forming a gel having at least one sample well.

6. A method according to claim 4 wherein said third upper plate is a wick area forming bar.

7. A method of casting a gel slab useful in electrophoretic procedures, comprising the steps of
   (a) forming a space having first and second opposing open edges between the facing surfaces of parallel horizontally positioned upper and lower plates separated a predetermined capillary action-inducing distance of from 0.25–3.5 mm apart;
   (b) introducing an acrylamide monomer solution into said space at one of said open edges whereby said solution is drawn into and fills said space by capillary action and is contained therein by surface tension; and
   (c) forming from said solution a polyacrylamide gel adhered to at least one of said surfaces.

8. A method of casting a plurality of gel salbs useful in electrophoretic procedures, comprising the steps of:
   (a) forming at least two spaces, each of said spaces having first and second opposing open edges between the facing surfaces of parallel horizontally positioned upper and lower plates separated a predetermined capelliary action-inducing distance apart,
   (b) introducing a gel forming liquid into each of said spaces at one of said open edges whereby said liquid is an amount substantially equal in volume to the volume of each said space along the entirety of each said first opposing edge in a manner which produces a front of said liquid, said front being drawn into each said space by capillary action thereby displacing and expelling air out of each said second opposing open edge and is contained therein by surface tension; and
   (c) forming from said liquid a gel adhered to at least of the surfaces of said spaces.

* * * * *